US012778799B2

(12) United States Patent
Codenotti et al.

(10) Patent No.: US 12,778,799 B2
(45) Date of Patent: Nov. 3, 2026

(54) VITREORETINAL SURGERY DEVICE

(71) Applicants: Marco Codenotti, Milan (IT); Lorenzo Iuliano, Cernusco sul Naviglio (IT)

(72) Inventors: Marco Codenotti, Milan (IT); Lorenzo Iuliano, Cernusco sul Naviglio (IT)

(73) Assignees: Marco Codenotii, Milan (IT); Lorenzo Iuliano, Cernusco sul Naviglio (IT)

( * ) Notice: Subject to any disclaimer, the term of this patent is extended or adjusted under 35 U.S.C. 154(b) by 652 days.

(21) Appl. No.: 17/921,780

(22) PCT Filed: Apr. 22, 2021

(86) PCT No.: PCT/IB2021/053317
§ 371 (c)(1),
(2) Date: Oct. 27, 2022

(87) PCT Pub. No.: WO2021/220109
PCT Pub. Date: Nov. 4, 2021

(65) Prior Publication Data

US 2023/0165712 A1 Jun. 1, 2023

(30) Foreign Application Priority Data

Apr. 27, 2020 (IT) ........................ 102020000009049

(51) Int. Cl.
*A61F 9/007* (2006.01)
*A61B 17/00* (2006.01)
*A61B 17/34* (2006.01)

(52) U.S. Cl.
CPC .... *A61F 9/007* (2013.01); *A61B 2017/00353* (2013.01); *A61B 17/3421* (2013.01)

(58) Field of Classification Search
CPC .. A61F 9/007; A61F 9/00727; A61F 9/00736; A61B 17/3421; A61B 2017/00353
See application file for complete search history.

(56) References Cited

U.S. PATENT DOCUMENTS 5,275,607 A * 1/1994 Lo ........................ A61F 9/00745 606/174
5,554,155 A * 9/1996 Awh .................... A61F 9/00736 604/289

(Continued)

FOREIGN PATENT DOCUMENTS

EP 0610247 A1 8/1994
WO WO-2017218610 A1 * 12/2017 ............ A61M 5/427

(Continued)

OTHER PUBLICATIONS

International Search Report and Written Opinion dated Aug. 6, 2021 from counterpart International Patent Application No. PCT/IB2021/053317.

*Primary Examiner* — Niketa Patel
*Assistant Examiner* — Karmel J Webster
(74) *Attorney, Agent, or Firm* — SHUTTLEWORTH & INGERSOLL, PLC; Timothy J. Klima

(57) ABSTRACT

A vitreoretinal surgery device includes a main body defining a receiving chamber therein and a needle or cannula provided with an inner longitudinal cavity in connection with said receiving chamber. The device includes a plurality of instruments, of which at least a first surgical instrument of elongated shape, and a second surgical instrument of elongated shape, and a selecting unit associated with the first and second surgical instruments, accommodated at least partially in said receiving chamber and configured to arrange the first surgical instrument in the operating position and the second surgical instrument in the resting position, or vice versa, upon a command given by a user.

11 Claims, 5 Drawing Sheets

(56) References Cited

U.S. PATENT DOCUMENTS

| | | | | |
|---|---|---|---|---|
| 6,592,541 | B1 * | 7/2003 | Kurwa ................ | A61F 9/00745 604/521 |
| 9,060,795 | B2 * | 6/2015 | Meenink ................ | A61B 34/74 |
| 2006/0241343 | A1 * | 10/2006 | Miller .............. | A61B 17/32053 600/106 |
| 2010/0057078 | A1 * | 3/2010 | Arts ....................... | A61B 18/24 606/1 |
| 2013/0237753 | A1 * | 9/2013 | Mark ..................... | A61B 1/018 600/104 |
| 2015/0148615 | A1 * | 5/2015 | Brennan .................. | A61B 3/16 128/853 |
| 2016/0015563 | A1 | 1/2016 | Humayun et al. | |

FOREIGN PATENT DOCUMENTS

| | | | | |
|---|---|---|---|---|
| WO | 2018081295 | A1 | 5/2018 | |
| WO | WO-2020101489 | A1 * | 5/2020 | ......... A61F 9/00763 |

* cited by examiner

VITREORETINAL SURGERY DEVICE

This application is the National Phase of International Application PCT/IB2021/053317 filed Apr. 22, 2021 which designated the U.S.

This application claims priority to Italian Patent Application No. 102020000009049 filed Apr. 27, 2020, which applications are incorporated by reference herein.

The present invention relates to a vitreoretinal surgery device.

The present invention finds particular application in the field of eye surgery, and more precisely, in the design and manufacture of surgical instruments adapted to be inserted into the eyeball to perform interventions aimed at the surgical treatment of diseases of the posterior part of the eye, in particular of the vitreous body and retina.

The basic principle of vitreoretinal surgery is based on the introduction of very thin instruments inside the eye, through some small incisions in the sclera, and on the maneuver thereof by the surgeon, who for obvious reasons can thus use a maximum of two instruments in the same operative moment.

During the operating step, the surgeon looks (with a microscope) inside the eye through the pupil, which is dilated with special eye drops, and while illuminating the operating area through a fiber optic torch held in one hand, performs the operations required by means of a special surgical instrument held in the other.

In this regard, however, it should be emphasized that typical vitreoretinal surgery requires the use of much more than one surgical instrument, often replaced and repeatedly used in different operating steps.

The surgeon uses different instruments, often used sequentially and more than once.

For this reason, every time a change in the type of maneuver is required, the surgeon is forced to extract the instrument in use, grip the new instrument (possibly passed by a scrub nurse), and finally reintroduce it into the eye.

This involves many problems, both of a purely temporal nature (longer operating times) and of a medical/surgical nature, since the replacement speed of an instrument is of crucial importance for a successful surgical outcome (example: in the event of hemorrhages or drainage of subretinal fluids) and for the stability of intraocular pressure.

Additionally, since the surgeon must necessarily look away for the introduction of the instrument and then return to the microscope in the operating step, the operator's sight during such long and complex operations suffers considerable fatigue, thereby limiting the number of interventions or the time spent in the operating room. Such an aspect is particularly noted in surgeons with refractive defects or presbyopia (surgeons over 45 years of age).

Therefore, it is the object of the present invention to provide a vitreoretinal surgery device which overcomes the aforementioned drawbacks of the known art.

In particular, it is the object of the present invention to provide a highly versatile and efficient vitreoretinal surgery device.

More precisely, it is the object of the present invention to provide a vitreoretinal surgery device which significantly reduces operating times and facilitates the instrument change for the surgeon.

Said objects are achieved by a vitreoretinal surgery device in accordance with the contents of the subsequent claims.

In particular, said objects are achieved by a vitreoretinal surgery device comprising a main body, a needle or cannula, and a plurality of surgical instruments.

Preferably, the main body (or handpiece) has an elongated shape extending along a longitudinal axis thereof between a first and a second end portion.

The main body is at least partially hollow inside and defines a receiving chamber therein.

The needle or cannula is connected to the main body and departs (or protrudes) away from the first end portion thereof up to a free end thereof.

The needle or cannula is also provided with an inner longitudinal cavity in connection with said receiving chamber and sized to receive at least one surgical instrument therein.

According to an aspect of the invention, the device comprises at least a first surgical instrument of elongated shape, at least a second surgical instrument of elongated shape, and a selecting unit associated with said first and second surgical instruments, accommodated at least partially in said receiving chamber and configured to arrange the first surgical instrument in the operating position and the second surgical instrument in the resting position, and vice versa, upon a command given by a user.

Therefore, the selecting unit is configured to move alternatively said first or said second surgical instrument from a resting position to an operating position upon a command given by a user.

Advantageously, the device is thereby a multi-instrument device in which there is only one needle or cannula which penetrates the sclera of the eye and in which two (or more) surgical instruments are slidably insertable.

This allows the surgeon to keep his gaze on the microscope for the entire duration of the operation, simply replacing the instrument in a simplified manner and without completely removing the needle from the sclera.

Such surgical instruments can be for example a vitrectome, a laser endophotocoagulation probe, vitreous forceps (of any type), a back-flush cannula for the exchange of intraocular fluids or gases, endovitreal forceps, spatulas.

Preferably, the first surgical instrument is provided with an active end portion thereof and is reversibly movable between a resting position, in which it is accommodated inside said receiving chamber, and an operating position, in which it is arranged crossing said inner longitudinal cavity with said active end portion protruding from the free end of the needle or cannula.

The second surgical instrument is also elongated in shape and has an active end portion thereof. The second surgical instrument is also reversibly movable between a resting position, in which it is accommodated inside said receiving chamber, and an operating position, in which it is arranged crossing said inner longitudinal cavity with said active end portion protruding from the free end of the needle or cannula.

Advantageously, when one of the two instruments is extracted and placed through the needle, the other remains accommodated in the receiving chamber, thus favoring the maneuverability of the device and not hindering the operations by the surgeon.

Therefore, the selecting unit is preferably configured alternatively to:

- move said first surgical instrument from the resting position to the operating position and the second surgical instrument from the operating position to the resting position upon receiving a first signal representative of a selection of said first surgical instrument;
- move said second surgical instrument from the resting position to the operating position and the first surgical instrument from the operating position to the resting position upon receiving a second signal representative of a selection of said second surgical instrument.

In this regard, the selecting unit comprises a control element arranged at least partially outside said main body and operable by the user (surgeon, assistant surgeon, scrub nurse) to generate said first and said second.

Preferably, the selecting unit comprises at least one thrust element associated with the first and second surgical instruments and movable parallel to said longitudinal axis between a retracted position and an extracted position, in which the first or second instrument is arranged in the operating position. In this regard, preferably the thrust element is substantially aligned with a central axis of said needle or cannula.

Furthermore, the selecting unit preferably comprises at least one drum provided with at least a first seat for receiving said first surgical instrument and at least a second seat for receiving said second surgical instrument.

This drum is movable between at least a first position, in which the first receiving seat is aligned with said needle or cannula, and a second position, in which the second receiving seat is aligned with said needle or cannula.

Therefore, the movement of the drum places the instrument required by the surgeon in alignment with the needle or cannula, while the thrust element translates it axially, positioning the active end portion thereof outside the needle or cannula (i.e., in the eye).

Therefore, in the operating position of the first surgical instrument, the drum is preferably positioned so that the first receiving seat is aligned with the needle or cannula and the thrust element associated with the first surgical instrument is arranged in an extracted position, at least partially accommodated inside said first receiving seat.

In the operating position of the second surgical instrument, the drum is positioned so that the second receiving seat is aligned with the needle or cannula and the thrust element associated with the second surgical instrument is arranged in an extracted position, at least partially accommodated inside said second receiving seat.

Operatively, the user (surgeon) thus operates the control element by generating the first signal or the second signal.

Following the generation of the first or second signal, the selecting unit positions the first or second surgical instrument in the operating position (and the second or first surgical instrument in the resting position), respectively.

More in detail, the thrust member is maintained or brought into the retracted position, so that the surgical instrument possibly connected thereto returns to the respective receiving seat.

At this point, the drum moves (e.g., rotates) to bring the receiving seat of the selected surgical instrument at the needle or cannula, or in alignment with the needle or cannula.

The thrust member is then grafted (or comes into contact) with said surgical instrument so as to push it linearly through the needle or cannula up to the operating position.

By means of the use of comprising a driving unit (e.g., pedal board), the surgeon can thus send a driving signal to an actuation member of the first or second surgical instrument, actuating it and thus performing the related maneuver during the operation.

In the case of a vitrectome, for example, the driving signal is representative of the movement of the blade and the suction pressure of the vitreous body.

Otherwise, in the case of a laser probe, the driving signal provides the command to switch on the laser.

Again, if the surgical instrument is a forceps, the driving signal (which can also be mechanical/analogue) is representative of the opening or closing of the arms.

These and other features, together with the related advantages, will become more apparent from the following exemplary non-limiting description of a preferred non-exclusive embodiment of a vitreoretinal surgery device as shown in the accompanying drawings, in which:

FIG. 1 shows a vitreoretinal surgery device according to the present invention, during use;

FIG. 2 diagrammatically shows a vitreoretinal surgery device according to the present invention, in a first embodiment;

Figure 5:
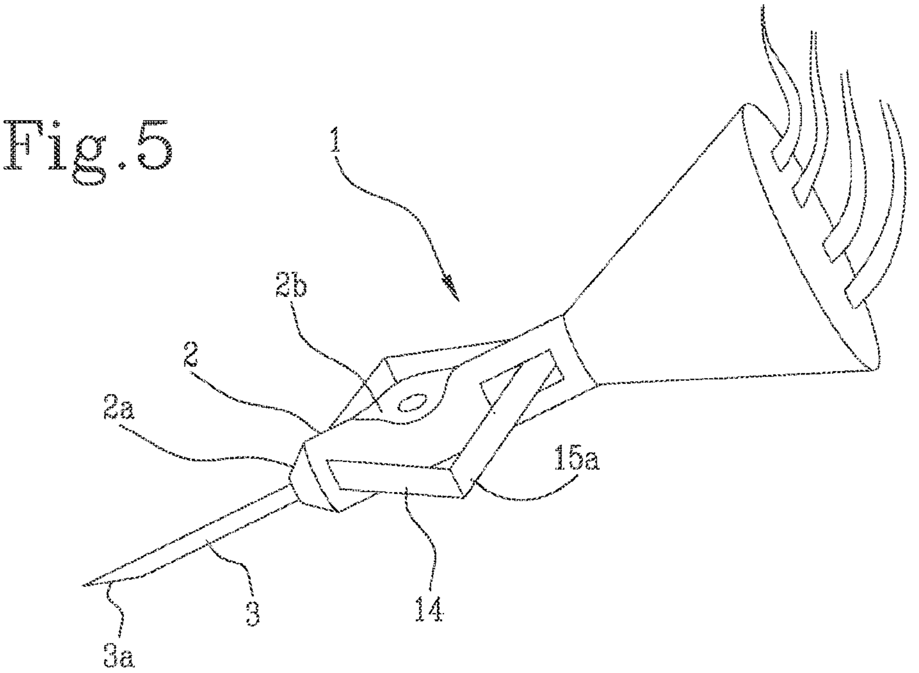
FIG. 5 shows a perspective view of a vitreoretinal surgery device according to the present invention, in a third embodiment.
Figure 9:
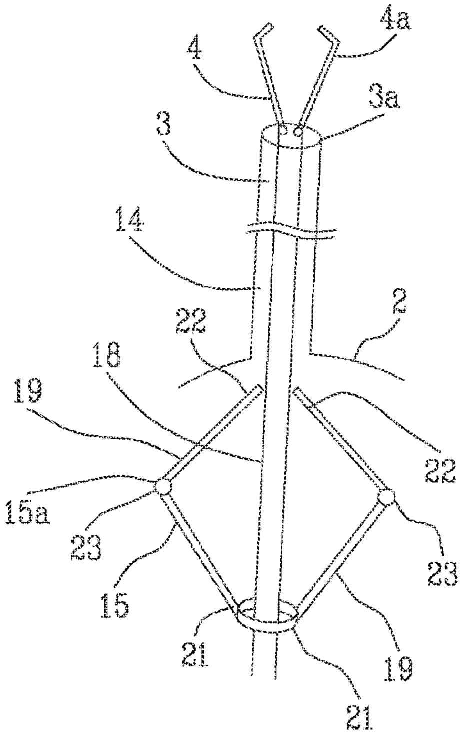
Figure 10:
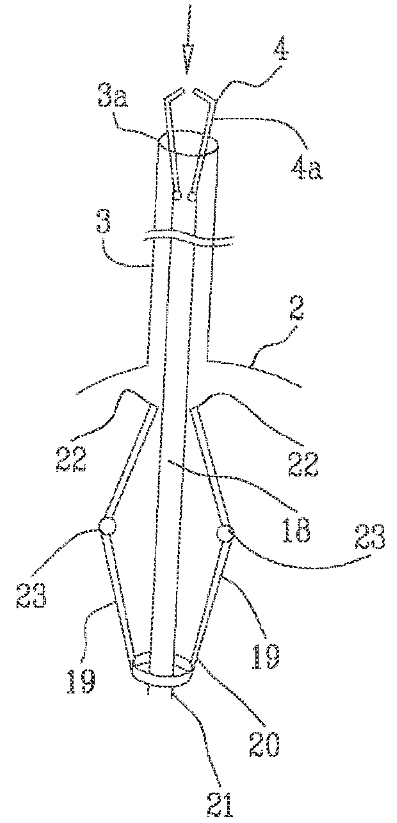
Figure 11:
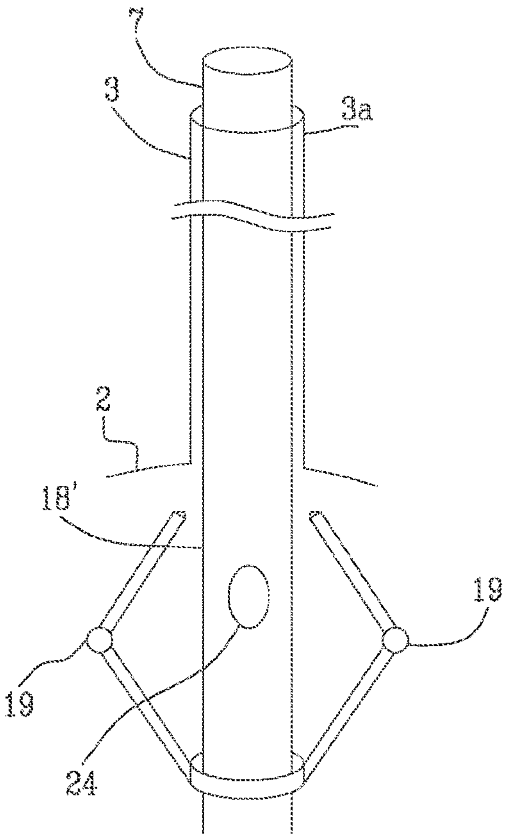
Figure 12:
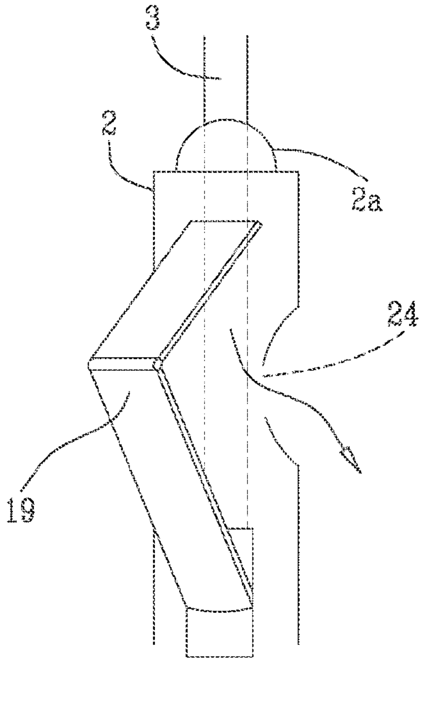

FIGS. 9-10 diagrammatically show a portion of the vitreoretinal surgery device in FIG. 5 in two different operating conditions;

FIG. 11 schematically shows the same portion of the vitreoretinal surgery device in FIG. 9 in a further operating condition;

FIG. 12 shows the same portion of the device in FIG. 11 in perspective and with some parts in phantom.

With reference to the accompanying drawings, reference numeral 1 indicates, as a whole, a vitreoretinal surgery device according to the present invention.

Such a device 1 thus belongs to the field of micro-invasive surgical instruments used to operate inside the eye.

The device 1 essentially comprises a main body 2, a needle or cannula 3 and a plurality of surgical instruments 3, 4, 5, 6.

The main body 2 has an elongated shape extending along a longitudinal axis "A" thereof between a first 2*a* and a second end portion.

The shape of the main body 2 is at least partially substantially cylindrical, possibly with a tapered end having dimensions such as to allow an easy grip by the surgeon or user "S".

Therefore, the main body 2 preferably has at least one grippable portion 2*b* having a substantially circular section, with a diameter of less than 5 cm.

The main body 2 is preferably at least partially hollow and defines a receiving chamber "C" therein.

The needle or cannula 3 instead has a tubular shape (i.e., hollow inside), with a diameter preferably less than 1 mm (approximately 19 gauge).

Therefore, such a needle or cannula 3 has an inner longitudinal cavity extending parallel to the longitudinal axis "A".

Such an inner longitudinal cavity is placed in connection with the receiving chamber "C".

The needle or cannula extends away from the first end portion 2*a* of the main body 2 to a free end 3*a* thereof.

Therefore, the needle or cannula 3 extends between a constrained end 3*b*, fixed to the main body 2 (in particular to the first end 2*a*), and the free end 3*a*.

Preferably, the free end 3*a* is tapered so as to define a tip which facilitates the penetration of the ocular sclera.

According to an aspect of the invention, the device comprises a plurality of surgical instruments 4, 5, 6, 7.

Therefore, the main body 2 has a plurality of seats 11*a*, 11*b*, 11*c*, 11*d* for receiving said plurality of surgical instruments 4, 5, 6, 7 therein.

Advantageously, this allows the surgeon to have a plurality of interchangeable surgical instruments located inside the single main body 2 and selectively extractable in an alternative manner as a function of the operative needs.

Each surgical instrument 4, 5, 6, 7 preferably has an elongated shape and is provided with an active end portion 4*a*, 5*a* thereof.

The surgical instruments 4, 5, 6, 7 are of the type used for vitreoretinal surgery and can be selected for example from those in the following list:

- endovitreal forceps of any type (for example: serrated, with internal limiting membrane, asymmetrical);
- vitrectome of any cutting speed or aspect (one-dimensional or two-dimensional);
- back-flush cannula, equally with silicone protection ("soft-tip") or without silicone protection ("blunt");
- laser endophotocoagulation probe;
- endodiathermy coagulator;
- endovitreal forceps (vertical or horizontal);
- spatulas or hooks ("pics").

According to a first embodiment, the device 1 comprises at least a first 4 and a second 5 surgical instrument.

Furthermore, in the preferred embodiment, the presence of a third 6 and/or a fourth 7 surgical instrument is also included.

In one of the preferred embodiments, the first surgical instrument 4 is defined by a vitrectome and the second surgical instrument 5 by a forceps.

Figure 3:
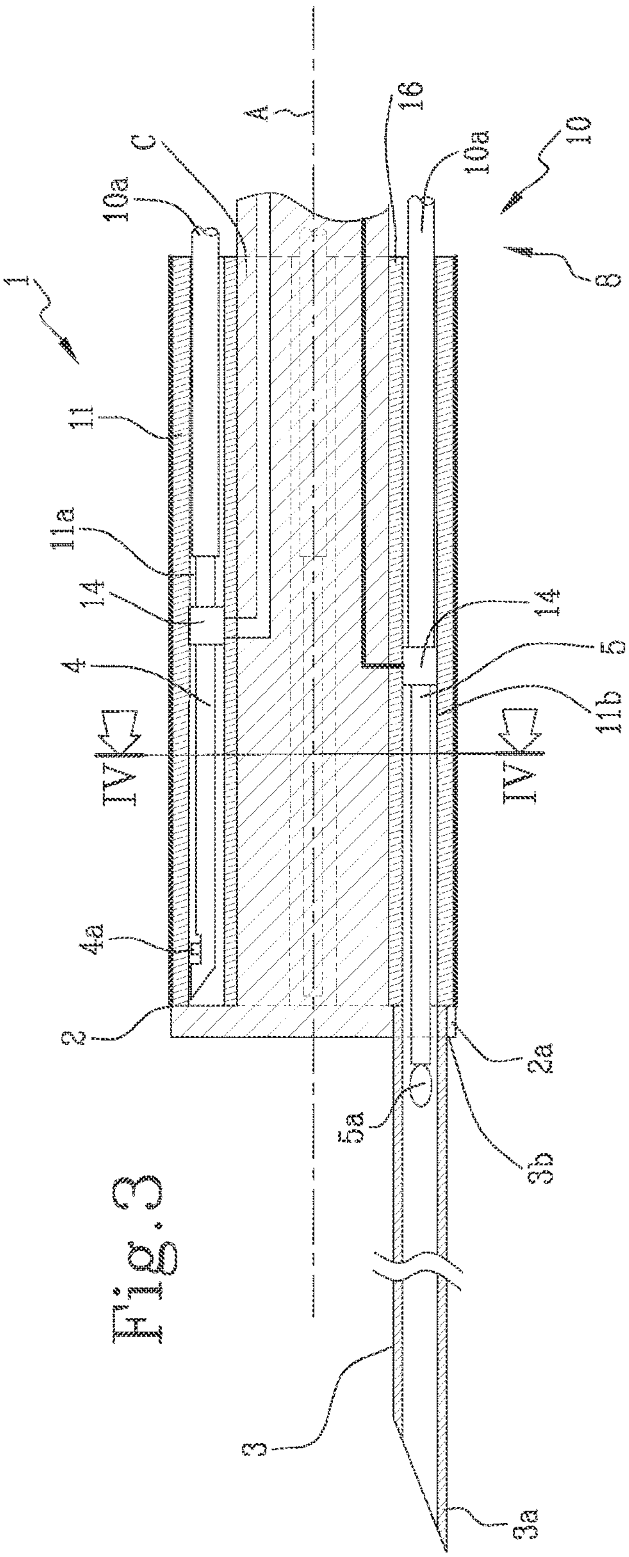
FIG. 3 shows a diagrammatic side view of a vitreoretinal surgery device according to the present invention, in a second embodiment and with some parts in phantom.
Figure 4:
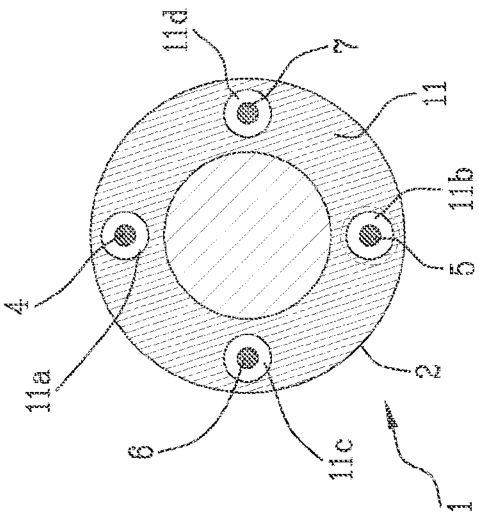
FIG. 4 shows a sectional view along section line IV-IV in FIG. 3.

With reference to FIGS. 3 and 4, a laser defining the third surgical instrument 6 and a back-flush cannula defining the fourth surgical instrument 7 are further shown.

Regardless of the nature thereof, all the surgical instruments 4, 5, 6, 7 are reversibly movable between a resting position, in which they are accommodated inside the receiving chamber "C", and an operating position, in which they are arranged crossing the inner longitudinal cavity of the needle or cannula 3, with said active end portion 4*a*, 5*a* protruding from the free end 3*a*.

It should be noted that when a surgical instrument is in the operating position, the other surgical instruments are necessarily in the respective resting position (or in an intermediate position, however not extracted from the needle or cannula).

Therefore, when the first surgical instrument 4 is in the operating position, with the active end portion 4*a* protruding from the free end 3*a*, the second surgical instrument 5 is placed in the resting position. Similarly, when the second surgical instrument 5 is in the operating position, with the active end portion 5*a* protruding from the free end 3*a*, the first surgical instrument 4 is placed in the resting position.

Furthermore, if present (as in FIG. 3), the third 6 and/or the fourth 7 surgical instrument are also in said resting position.

Likewise, such third 6 and/or fourth 7 surgical instruments, if present, can be placed in the operating position only with the other instruments in the resting position.

To this end, the device 1 preferably comprises a selecting unit 8 associated with said surgical instruments 4, 5, 6, 7.

The selecting unit 8 is accommodated at least partially in the receiving chamber "C" and is configured to alternatively arrange one of the surgical instruments 4, 5, 6, 7 in the operating position upon a command given by a user "5".

In particular, the selecting unit 8 is configured to move a surgical instrument 4, 5, 6, 7 to the operating position, keeping the others in the resting position.

Therefore, the selecting unit 8 is preferably configured to arrange one of the surgical instruments 4, 5, 6, 7 in the operating position and the remaining (one or more) surgical instruments in the resting position upon receiving a signal (analog or digital) representative of the selection of said surgical instrument.

For example, in embodiments with two surgical instruments, the selecting unit 8 is associated with the first 4 and second 5 surgical instrument and is configured to arrange the first surgical instrument 4 in the operating position and the second surgical instrument 5 in the resting position, or vice versa, upon a command given by the user "S".

More precisely, the selecting unit 8 is thus configured to move the first surgical instrument 4 from the resting position to the operating position and the second surgical instrument 5 from the operating position to the resting position upon receiving a first signal representative of a selection of said first surgical instrument 4.

Furthermore, the selecting unit 8 is configured to move the second surgical instrument 5 from the resting position to the operating position and the first surgical instrument 4 from the operating position to the resting position upon receiving a second signal representative of a selection of said second surgical instrument.

In embodiments with more than two surgical instruments, an example of which is shown in FIGS. 3 and 4, the selecting unit 8 is associated with the first 4, the second 5, the third 6 and/or the fourth 7 surgical instrument and is configured to:

- arrange the first surgical instrument 4 in the operating position and the second 5, third 6 and/or fourth 7 surgical instruments in the resting position, upon receiving a first signal representative of a selection of said first surgical instrument 4;
- arrange the second surgical instrument 5 in the operating position and the first 4, third 6 and/or fourth 7 surgical instruments in the resting position, upon receiving a second signal representative of a selection of said second surgical instrument 4;
- arrange the third surgical instrument 6 in the operating position and the first 4, second 5 and fourth 7 surgical instruments (if present) in the resting position, upon receiving a third signal representative of a selection of said third surgical instrument 6;
- if present, arrange the fourth surgical instrument 7 in the operating position and the first 4, second 5 and third 6 surgical instruments in the resting position, upon receiving a fourth signal representative of a selection of said fourth surgical instrument 7.

In this regard, the selecting unit 8 comprises a control element 9 arranged at least partially outside the main body 2 and operable by the user "S" (surgeon himself, assistant, scrub nurse) to generate the signals representative of the surgical instruments 4, 5, 6, 7 selected.

The control element 9 can be defined by a mechanical actuator which can be operated manually by the surgeon (e.g., FIG. 2) or by an electronic or electromechanical transducer capable of transforming the surgeon's action into an analog or digital signal.

In the preferred embodiment, the control element 9 is a button configured to generate a related signal representative of the selection of a surgical instrument 4, 5, 6, 7.

Preferably, the selecting unit 8 comprises at least a first actuator 10 partially movable parallel to said longitudinal axis "A" between a retracted position and an extracted position.

Preferably, the first actuator 10 comprises at least one thrust element 10*a* movable parallel to said longitudinal axis "A" between the retracted position and the extracted position.

In the retracted position, the thrust element 10*a* is placed in a distal position from the first end portion 2*a* of the main body 2 and places the surgical instrument 4, 5, 6, 7 in the resting position, or at least allows the placement thereof in such a position.

In the extracted position, the thrust element 10*a* is instead located near the first end portion 2*a* of the main body 2.

In such an extracted position, the thrust element 10*a* is located/configured so as to arrange the surgical instrument 4, 5, 6, 7 associated therewith in the operating position.

It should be noted that the first actuator 10 is configured so as to actively act (i.e., in thrust) on a single surgical instrument, without directly acting on the others.

In this regard, the first actuator 10 can comprise a single thrust element 10*a*, configured to alternatively couple with only one of the surgical instruments (for example with the first 4 or with the second 5 surgical instrument).

In this embodiment, the thrust element 10*a* comprises a trigger configured to reversibly couple with each of the surgical instruments 4, 5, 6, 7.

Preferably, the thrust element 10*a* is configured to couple with an end (or end portion) of the surgical instrument opposite the end portion 4*a*, 5*a*.

With reference to the embodiment in FIGS. 5-8, for example, the device could comprise a single thrust (or traction) element 10*a* arranged coaxially to said needle or cannula 3 and configured to couple with each of the surgical instruments 4, 5, 6, 7 as a function of a command given by the user "S".

In such an embodiment, for example, the first actuator 10 comprises a thrust element 10*a* movable between the retracted position and the extracted position and a gripping unit configured to couple with each instrument previously placed coaxially to the needle or cannula 3. Alternatively, as shown in FIGS. 2, 3, 4, the first actuator 10 comprises a plurality of thrust elements 10*a* each associated with a respective surgical instrument 4, 5, 6, 7.

Figure 2:
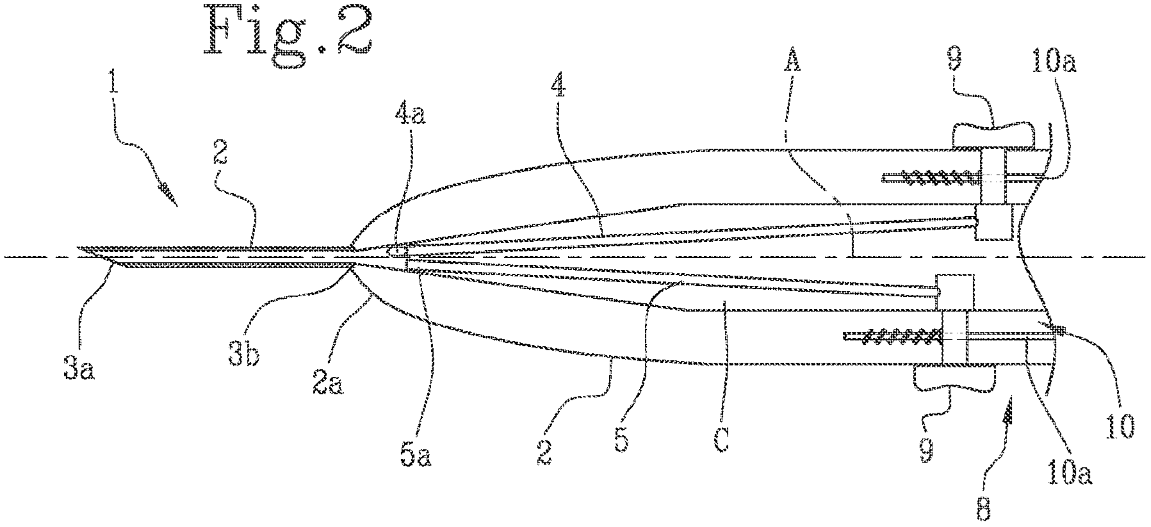

With reference to FIG. 2, the first actuator 10 comprises two thrust elements 10*a* associated with the first 4 and the second 5 surgical instruments, respectively.

With reference to the embodiment shown in FIGS. 3 and 4, the first actuator 10 instead comprises four thrust elements 10*a* associated with the first 4, the second 5, the third 6, and the fourth 7 surgical instruments, respectively.

In such embodiments, all the thrust elements 10*a* are movable between the retracted position and the extracted position in a mutually exclusive manner.

In other words, when a thrust element 10*a* is in the extracted position, the other thrust elements 10*a* are in the retracted position.

It should be noted that, preferably, each thrust element 10*a* is, in at least one operating position thereof, aligned with a central axis of said needle or cannula 3.

In other words, each thrust element 10*a* is movable from the retracted position to the extracted position (and vice versa) only if aligned with the central axis of said needle or cannula 3.

Advantageously, the movement of the surgical instrument 4, 5, 6, 7 does not thus stress the structure thereof, to the full advantage of the operating precision and reliability of the device 1. It should be noted that, preferably, the first actuator 10 is configured to move each surgical instrument 4, 5, 6, 7 from an intermediate position to the operating position, in which the intermediate position is precisely located along a movement path of the surgical instrument 4, 5, 6, 7 between the resting position and the operating position.

Therefore, the selecting unit 8 preferably comprises a second actuator 16, configured to move each surgical instrument 4, 5, 6, 7 from the resting position to the intermediate position.

In some embodiments, the second actuator 16 of the selecting unit 8 is configured to move all the surgical instruments 4, 5, 6, 7 along a movement path with several stations or steps; at each station or step one of the surgical instruments 4, 5, 6, 7 is placed in the respective intermediate position, aligned with the needle or cannula 3.

An example of such embodiments is shown in FIGS. 3 and 4, in which the selecting unit 8 comprises at least one drum 11 provided with said plurality of receiving seats 11*a*, 11*b*, 11*c*, 11*d*.

Therefore, the drum 11 has at least a first receiving seat 11 a and a second receiving seat 11*b* for the first 4 and the second surgical instruments, respectively.

In the preferred embodiment, the drum 11 also has a third receiving seat 11*c* and a fourth receiving seat 11*d* for the third 6 and the fourth 7 surgical instruments, respectively.

Preferably, the second actuator 16 is configured to move the drum 11 between several positions corresponding to said stations or steps which in number are at least equal to the number of surgical instruments 4, 5, 6, 7; as said, each position is such as to align the respective seat for receiving the surgical instrument with the needle or cannula 3 in order to allow the instrument to be extracted and retracted.

More precisely, the second actuator 16 is configured to receive the signal representative of the surgical instrument 4, 5, 6, 7 selected by the surgeon (generated by the control element 9) and to move the drum 11 upon receiving said signal.

Preferably, each representative signal corresponds to a position of the drum 11 in which the seat for receiving the selected surgical instrument is aligned with the needle or cannula 3.

Therefore, the drum 11 is preferably movable between at least a first position, in which the first receiving seat 11*a* is aligned with said needle or cannula 3 and at least a second position, in which the second receiving seat 11*b* is aligned with the needle or cannula 3.

In the preferred embodiment, shown in FIGS. 3 and 4, the drum 11 is movable between at least:

- a first position, in which the first receiving seat 11*a* is aligned with the needle or cannula 3;
- a second position, in which the second receiving seat 11*b* is aligned with the needle or cannula 3;
- a third position, in which the third receiving seat 11*c* is aligned with the needle or cannula 3;
- a fourth position, in which the second receiving seat 11*d* is aligned with the needle or cannula 3.

Preferably, the drum 11 is rotatably accommodated in the main body 2 so as to rotate around said longitudinal axis "A".

Therefore, the positions of the drum 11 are preferably angular positions.

Therefore, in the preferred embodiment the second actuator 16 is of the rotary type.

Preferably, the drum 11 has a central portion 12, coaxial to the longitudinal axis "A", and a peripheral portion 13, provided with said receiving seats 11*a*, 11*b*, 11*c*, 11*d*.

In this regard, it should be noted that the drum 11 can be substantially cylindrical, with a markedly distinct central and peripheral portion, or substantially annular, with a very close central and peripheral portion (see FIGS. 3 and 4).

Advantageously, the drum can thereby easily rotate in a plurality of angular positions, each corresponding to an operating position in which the thrust element 10*a* can move from the retracted position to the extracted position and, consequently, the corresponding surgical instrument 4, 5, 6, 7 can move from the resting position to the operating position.

Therefore, in the operating position of the first surgical instrument 4, the drum 11 is positioned so that the first receiving seat 11*a* is aligned with the needle or cannula 3 and the related thrust element 10*a* is arranged in the extracted position, at least partially accommodated inside said first receiving seat 11*a*.

In the operating position of the second surgical instrument 5, the drum 11 is positioned so that the second receiving seat 11*b* is aligned with the needle or cannula 3 and the related thrust element 10*a* is arranged in the extracted position, at least partially accommodated inside said second receiving seat 11*b*.

In the operating position of the third surgical instrument 6 (if present), the drum 11 is positioned so that the third receiving seat 11*c* is aligned with the needle or cannula 3 and the related thrust element 10*a* is arranged in the extracted position, at least partially accommodated inside said third receiving seat 11*c*.

In the operating position of the fourth surgical instrument 7 (if present), the drum 11 is positioned so that the fourth receiving seat 11*d* is aligned with the needle or cannula 3 and the related thrust element 10*a* is arranged in the extracted position, at least partially accommodated inside said second fourth seat 11*d*.

The seats for receiving the non-operating surgical instrument(s) (i.e., in the resting position) are instead preferably offset with respect to the needle or cannula 3, or misaligned with respect to said needle or cannula 3.

Preferably, the receiving seats of the non-operating surgical instrument(s) are angularly offset with respect to the needle or cannula by an angle equal to the angular offset of each receiving seat with respect to that aligned with the needle or cannula 3.

In the preferred embodiment, the drum 11 is centrally pivoted to the main body 2 to rotate internally thereto around the rotation axis thereof, preferably corresponding to the longitudinal axis.

Preferably, moreover, the receiving seats 11*a*, 11*b*, 11*c*, 11*d* are angularly equidistant to each other around the rotation axis.

In this regard, the selecting unit 8 comprises an actuation system (not shown) configured to move the drum 11 to the various positions.

In alternative embodiments, the second actuator 16 is instead configured to individually move each surgical instrument 4, 5, 6, 7 from the resting position to the intermediate position (and vice versa), without moving the others.

In other words, the second actuator 16 can be configured to act on a single surgical instrument 4, 5, 6, 7 at a time, bringing the de-selected instrument from the intermediate position to the resting position in succession and the selected one from the resting position to the intermediate one.

Figure 6:
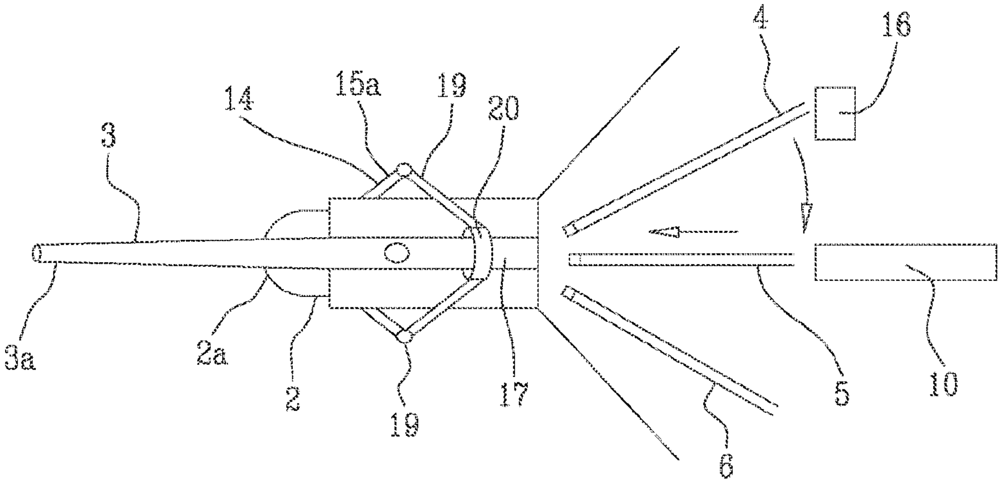
FIG. 6 shows a diagrammatic side view of the vitreoretinal surgery device in FIG. 5.
Figure 7:
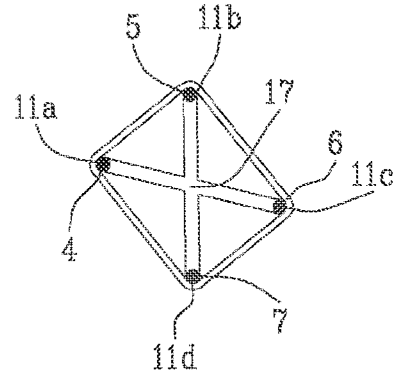
FIGS. 7-8 show portions of the vitreoretinal surgery device in FIG. 5.
Figure 8:
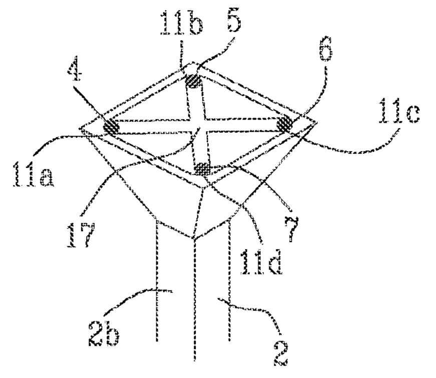

An example of such an embodiment is shown in FIGS. 5 and 6, in which the seats 11*a*, 11*b*, 11*c*, 11*d* of the surgical instruments 4, 5, 6, 7 are obtained in the main body 2 and are all connected with a single channel 17 (preferably central) aligned with the needle or cannula 3. Such a channel 17 thus corresponds to the intermediate position.

Therefore, in such an embodiment the second actuator 16 is configured to withdraw each surgical instrument 4, 5, 6, 7 from the receiving seat 11*a*, 11*b*, 11*c*, 11*d* thereof and to position it in said channel 17 (and vice versa); the thrust element 10*a* is then designed to axially translate the surgical instrument 4, 5, 6, 7 selected into the operating position by moving it from the retracted position to the extracted position.

In the embodiment shown, each surgical instrument 4, 5, 6, 7 in the resting position is arranged in the receiving seat, inclined with respect to the longitudinal axis "A" so that the end portion 4*a*, 5*a* is proximal to the axis. The actuation system is thus configured to rotate (i.e., tilt) the selected surgical instrument 4, 5, 6, 7 until it is aligned with the channel 17, in an intermediate position. The thrust element 10*a* is thus configured to couple with the instrument in the intermediate position and bring it, moving towards the extracted position, to the operating position.

Regardless of the type of selecting unit 8, each surgical instrument 4, 5, 6, 7 preferably comprises an actuation member 14 configured to drive the respective surgical instrument upon receiving a driving signal "DS".

Such an actuation member 14 can be of various nature and location according to the type of surgical instrument; for example, the actuation member 14 can be defined by:

- a pneumatic system of suction and movement of the cutting blade of the vitreous body (for a vitrectome);
- a movement system, which can be mechanical and integrated in the main body 2 or electromechanical/pneumatic arranged partially remotely with respect to the main body 2 (for example for the arms of a forceps or endovitreal forceps);
- a laser energy transfer system (for the laser probe);
- a communication system with the external environment which can be occluded by the surgeon's hand (for the backflush cannula);
- an electrical resistor system, capable of supplying heat (for the diathermocoagulator).

In order to control the actuation members 14, the device 1 comprises a driving system 15 operatively associated with the actuation member of each surgical instrument 4, 5, 6, 7 and configured so as to send said (analog or digital) driving signal "DS" to said actuation member 14 upon a command given by the user "S" (i.e., surgeon).

Such a driving system 15 can be of an electromechanical, pneumatic, or purely mechanical nature, and can be located locally at the main body 2, in a remote position or partially in both positions.

The driving system 15 preferably comprises at least an interface member 15*a* configured to detect a command by the user "S" and to generate a representative signal of said command "CS".

The interface member 15*a* can be of various kinds, either integrated in the main body 2 or separated therefrom.

As previously mentioned, for some surgical instruments (e.g., forceps), the interface member 15*a* is associated with the main body 2 and directly determines the actuation of the respective driving member 14.

For example, as shown in FIGS. 9-10 for an endovitreal forceps, the driving member 14 comprises a tubular member 18 containing the tool (forceps) and slidingly associated therewith so as to activate it (e.g., when opening or closing) following a relative axial movement between the tubular member and the tool.

In such an embodiment, the interface member 15*a* is preferably defined by at least one pair of arms 19 (preferably two pairs) which can be connected to the related surgical instrument at least when it is in the intermediate position.

The two arms 19 comprise a fixed hinge 22 and a movable joint 23 such that, following the application of a transversal/orthogonal pressure to the longitudinal axis "A", the angle between the arms 19 increases, translating a ring 20 fitted on the tubular member 18.

The tubular member 18 is in turn provided with an abutment shoulder 21 which, following a pressure from the ring 20, causes a corresponding translation of the tubular member 18 itself and a consequent movement of the tool.

It should be noted that any further tools could be provided with similar tubular members but without abutment shoulders, so that any possible movement of the arms has no effect on the tool.

Figure 1:
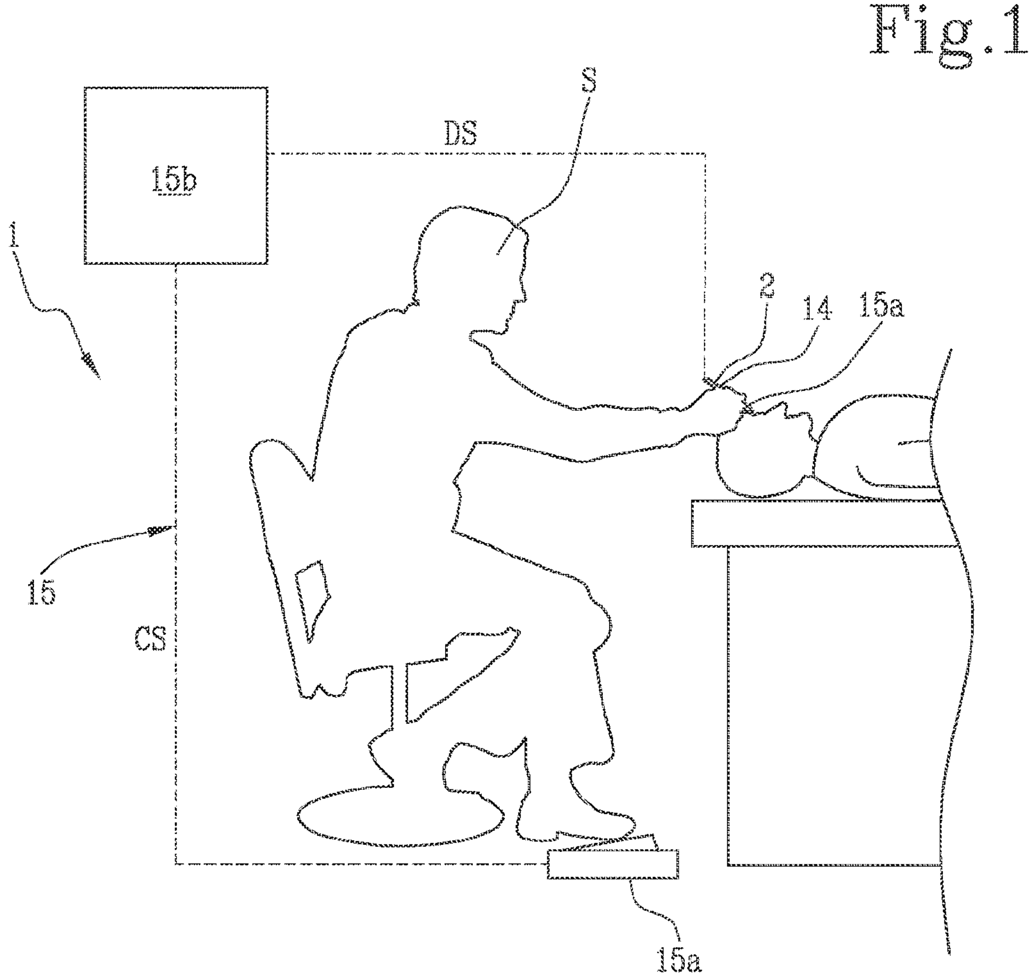

For further types of surgical instruments, the interface member 15*a* could be a pedal board provided with a plurality of pedals each configured to generate a special command signal "CS" (see FIG. 1 in this regard).

In such a configuration, the driving system 15 further comprises a control unit 15*b* configured to receive said representative signal "CS" and to generate said driving signal "DS".

It should be noted that in some cases the driving system 15 could be hybrid, in part controlled by a remote interface member 15*a* (e.g., pedal board) and in part by an interface member 15*a* located on the main body 2.

This is the case, for example, of surgical instruments such as the back-flush cannula 7 (FIG. 11-12), in which the tubular member 18' could lack the abutment described above but provided with an orifice 24 which, in the operating position, is facing and aligned with a corresponding opening 25 made on the main body 2, preferably at the grippable portion 2*b*, and appropriately sealed thereto (for example by a silicone ring), to allow the user "S" to vary the pressure inside the tubular member 18' by occluding or not occluding the opening 25 (and therefore the orifice 24).

It should be noted that the control element 9 could be integrated in the main body 2 or in the interface member 15*a*, or still in a further component of the device 1, falling in all cases within the spirit of the present invention.

The invention achieves the intended purposes and achieves important advantages.

In fact, the provision of a device which integrates a plurality of interchangeable surgical instruments without removing the needle from the eye greatly facilitates the instrument change operations during surgery, reducing the time of the operation and significantly reducing the fatigue of the surgeon.

The invention claimed is:

1. A vitreoretinal surgery device, comprising:

a handpiece having an elongated shape extending along a longitudinal axis thereof between a first and a second end portion and defining a receiving chamber therein;

a single needle or cannula configured to penetrate the sclera of an eye to be treated and departing away from said first end portion up to a free end thereof and including an inner longitudinal cavity in connection with said receiving chamber;

at least a first surgical instrument of elongated shape and including an active end portion thereof; said first surgical instrument being reversibly movable between a resting position, in which the first surgical instrument is accommodated inside said receiving chamber, and an operating position, in which the first surgical instrument is arranged crossing said inner longitudinal cavity with said active end portion protruding from the free end of the single needle or cannula;

at least a second surgical instrument of elongated shape and including an active end portion thereof; said second surgical instrument being reversibly movable between a resting position, in which the second surgical instrument is accommodated inside said receiving chamber, and an operating position, in which the second surgical instrument is arranged crossing said inner longitudinal cavity with said active end portion protruding from the free end of the single needle or cannula;

a selecting unit operatively connected with said first and second surgical instruments, accommodated at least partially in said receiving chamber and configured to arrange the first surgical instrument in the operating position and the second surgical instrument in the resting position, and vice versa, upon a command given by a user, wherein said selecting unit comprises:

at least one rotatable drum including at least a first receiving seat for receiving said first surgical instrument and at least a second receiving seat for receiving said second surgical instrument and selectively rotatable about said longitudinal axis between at least a first angular position, in which the first receiving seat is aligned with said single needle or cannula, and at least a second angular position, in which the second receiving seat is aligned with said single needle or cannula;

at least a first actuator operatively connected with the first and the second surgical instruments to move said first and second surgical instruments parallel to said longitudinal axis between a retracted position, in which the first or the second surgical instrument is located within the relative first or second receiving seat of the rotatable drum, and an extracted position, corresponding to said operating position;

at least a second actuator configured to rotate the rotatable drum at least between the first and second angular positions to move each of the first and second surgical instruments between the resting position and an intermediate position, corresponding to said retracted position, or vice versa.

2. The vitreoretinal surgery device according to claim 1, wherein said selecting unit is alternatively configured to:

move said first surgical instrument from the resting position to the operating position and the second surgical instrument from the operating position to the resting position upon receiving a first signal representative of a selection of said first surgical instrument;

move said second surgical instrument from the resting position to the operating position and the first surgical instrument from the operating position to the resting position upon receiving a second signal representative of a selection of said second surgical instrument.

3. The vitreoretinal surgery device according to claim 2, wherein said selecting unit comprises a control element arranged at least partially outside said handpiece and operable by the user to generate said first and said second signals.

4. The vitreoretinal surgery device according to claim 1, wherein said first actuator comprises at least one thrust element substantially aligned with a central axis of said single needle or cannula.

5. The vitreoretinal surgery device according to claim 4, wherein:

in the operating position of the first surgical instrument, the rotatable drum is positioned in the first angular position and the thrust element operative with the first surgical instrument is arranged in an extracted position, at least partially accommodated inside said first receiving seat;

in the operating position of the second surgical instrument, the rotatable drum is positioned in the second angular position and the thrust element operative with the second surgical instrument is arranged in an extracted position, at least partially accommodated inside said second receiving seat.

6. The vitreoretinal surgery device according to claim 1, wherein said first and second surgical instruments are two of the following:

endovitreal forceps of any type;

vitrectome of any cutting speed or aspect;

back-flush cannula, with silicone protection or without silicone protection;

straight-laser endophotocoagulation probe;

endodiathermy coagulator;

endovitreal forceps;

spatulas or hooks.

7. The vitreoretinal surgery device according to claim 1, wherein each of the first or second surgical instruments comprises an actuation member configured to drive the respective one of the first and second surgical instruments upon receiving a driving signal.

8. The vitreoretinal surgery device according to claim 7, and further comprising a driving system operatively connected with each actuation member of the first and second surgical instruments, and configured to send said driving signal to the respective actuation member upon a command given by the user.

9. The vitreoretinal surgery device according to claim 8, wherein said driving system comprises at least one interface member configured to detect a command by the user and to generate a representative signal of said command.

10. The vitreoretinal surgery device according to claim 8, wherein said driving system comprises a control unit configured to receive said representative signal and to generate said driving signal.

11. The vitreoretinal surgery device according to claim 1, and further comprising a third and/or fourth surgical instrument arranged, respectively, in a third and/or a fourth receiving seat located in said handpiece.

* * * * *